(12) United States Patent
Abebe et al.

(10) Patent No.: US 10,338,007 B2
(45) Date of Patent: Jul. 2, 2019

(54) SYSTEM AND METHOD FOR DETECTING PACKAGE TAMPERING

(71) Applicant: International Business Machines Corporation, Armonk, NY (US)

(72) Inventors: Ermyas Abebe, Carlton (AU); Brendan Haesler, Heidelberg (AU); Dileban Karunamoorthy, Carlton (AU); Lenin Mehedy, Doncaster East (AU)

(73) Assignee: International Business Machines Corporation, Armonk, NY (US)

( * ) Notice: Subject to any disclaimer, the term of this patent is extended or adjusted under 35 U.S.C. 154(b) by 110 days.

(21) Appl. No.: 15/440,688

(22) Filed: Feb. 23, 2017

(65) Prior Publication Data

US 2018/0238817 A1    Aug. 23, 2018

(51) Int. Cl.
*G01N 21/956* (2006.01)
*G01N 21/90* (2006.01)
*G01N 21/88* (2006.01)

(52) U.S. Cl.
CPC ... *G01N 21/95607* (2013.01); *G01N 21/8851* (2013.01); *G01N 21/90* (2013.01)

(58) Field of Classification Search
CPC .................................................. G01N 21/956
(Continued)

(56) References Cited

U.S. PATENT DOCUMENTS 5,443,171 A    8/1995  Sprowl
9,037,421 B2 *  5/2015  Jones ...................... G01M 3/38
                                                  702/51
(Continued)

FOREIGN PATENT DOCUMENTS

CN    201447130 U    5/2010
CN    204009979 U    12/2014
(Continued)

OTHER PUBLICATIONS thefutureofthings.com, "Hitachi Develops World's Smallest RFID Chip," http://thefutureofthings.com/3221-hitachi-develops-worlds-smallest-rfid-chip/ Nov. 8, 2016, 3 pages.

Harald Vogt, "Multiple Object Identification with Passive RFID Tags," IEEE International Conference on Systems, Man and Cybernetics, 2002, 6 pages.

(Continued)

*Primary Examiner* — Tarifur R Chowdhury
*Assistant Examiner* — Omar H Nixon
(74) *Attorney, Agent, or Firm* — Grant Johnson; Ryan, Mason & Lewis, LLP (57) ABSTRACT

A method for detecting package tampering comprises performing first scanning of a container comprising a packaged item and a plurality of packaging elements surrounding the packaged item, wherein each of the plurality of packaging elements comprises an identification component, and the first scanning comprises using the identification component of each of the plurality of packaging elements to detect each of the plurality of packaging elements. The method further comprises determining an orientation of each of the plurality of packaging elements in the container from the first scanning, performing second scanning of the container, determining an orientation of each of the plurality of packaging elements in the container from the second scanning, and comparing the orientation of each of the plurality of packaging elements in the container from the first scanning with the orientation of each of the plurality of packaging elements in the container from the second scanning.

22 Claims, 6 Drawing Sheets

(58) Field of Classification Search
USPC .................................................. 356/240.01
See application file for complete search history.

(56) References Cited

U.S. PATENT DOCUMENTS

| | | |
|---|---|---|
| 2002/0177490 A1 | 11/2002 | Yong et al. |
| 2004/0215480 A1* | 10/2004 | Kadaba ............... B07C 3/00 705/338 |
| 2005/0099292 A1* | 5/2005 | Sajkowsky ........... G06K 17/00 340/539.13 |
| 2008/0247098 A1 | 10/2008 | Deak |
| 2011/0251969 A1 | 10/2011 | Gago et al. |
| 2013/0197832 A1* | 8/2013 | Jones ................... G01M 3/38 702/51 |
| 2014/0182394 A1 | 7/2014 | Pagani et al. |
| 2015/0067346 A1 | 3/2015 | Ross et al. |
| 2016/0001952 A1 | 1/2016 | Kulkarni et al. |
| 2016/0239802 A1* | 8/2016 | Burch .................. H04W 4/70 |

FOREIGN PATENT DOCUMENTS

| | | |
|---|---|---|
| CN | 204078258 U | 1/2015 |
| EP | 2869240 A2 | 5/2015 |
| WO | 2012131704 A2 | 10/2012 |
| WO | 2014132268 A2 | 9/2014 |

OTHER PUBLICATIONS www.packaging-gateway.com, "Weird Science: Using DNA Authentication to Fight Counterfeit Packaging," http://www.packaging-gateway.com/features/featureweird-science-dna-authentication-counterfeit-packaging, Jul. 26, 2012, 4 pages.
www.iom3.org, "Biometric Fingerprints for Anti-Counterfeiting," http://www.iom3.org/packaging-professional-magazine/news/2007/jul/01/biometric-fingerprints-anticounterfeiting, Nov. 9, 2016, 2 pages.
S. Vasudevan et al., "On Neighbor Discovery in Wireless Networks with Directional Antennas," ftp://ftp.cs.umass.edu/pub/net/pub/Vasudevan04_NeighborDiscovery.pdf, UMass Computer Science Technical Report 04-53, 2005, 24 pages.
opencv.org, "OpenCV (Open Source Computer Vision)," http://opencv.org/, Nov. 9, 2016, 3 pages.
scikit-image.org, "Image Processing in Python," http://scikit-image.org, Nov. 9, 2016, 2 pages.
Dongfeng Zhang, "A Nano-Tensile Testing System for Studying Nanostructures Inside an Electron Microscope: Design, Characterization and Application," PhD Thesis, https://infoscience.epfl.ch/record/142931/files/EPFL_th4605.pdf, Mar. 2010, 152 pages.
Henrik Mindedal, "A Micro-Miniature Sensor for In Vivo Pressure Measurement," Sensors Magazine, http://www.sensorsmag.com/specialty-markets/medical/a-micro-miniature-sensor-in-vivo-pressure-measurement-1326, Jan. 1, 2007, 2 pages.
Suzanne Smiley, "Active RFID vs. Passive RFID: What's the Difference," http://blog.atlasrfidstore.com/active-rfid-vs-passive-rfid, Mar. 4, 2016, 14 pages.
Z. Shelby et al., "Neighbor Discovery Optimization for Low-Power and Lossy Networks," draft-ietf-6lowpan-nd-12, Aug. 3, 2010, 50 pages.
List of IBM Patents or Patent Applications Treated as Related.

* cited by examiner

SYSTEM AND METHOD FOR DETECTING PACKAGE TAMPERING

BACKGROUND

Typically, customers, when shipping items through one or more intermediaries, such as, for example, shipping services, want assurance of the integrity of the items, and will hold an intermediary accountable if the items are tampered with or lost. A package shipped nationally or internationally may be subject to tampering at various locations throughout its route, including for example, at a manufacturing facility, initial and intermediate shipping facilities, distribution facilities and point of sale locations. Some products of a relatively sensitive nature that are shipped, including, for example, pharmaceuticals, toys, and automotive and aircraft parts can cause harmful health and/or safety risks if tampered with.

Known attempts at preventing loss and/or tampering of packages include labeling or tagging the outside of a package. Such labeling or tagging techniques including, for example, bar codes, holographic labels, radio frequency identification (RFID) tags, etc., have been used with some success. However, these codes, labels, tags, etc., can be lost, stolen or duplicated, since they are located on the outside of a package.

SUMMARY

According to an exemplary embodiment of the present invention, a method for detecting package tampering comprises performing first scanning of a container comprising a packaged item and a plurality of packaging elements surrounding the packaged item, wherein each of the plurality of packaging elements comprises an identification component, and the first scanning comprises using the identification component of each of the plurality of packaging elements to detect each of the plurality of packaging elements. The method further comprises determining an orientation of each of the plurality of packaging elements in the container from the first scanning, performing second scanning of the container comprising the packaged item and the plurality of packaging elements surrounding the packaged item, determining an orientation of each of the plurality of packaging elements in the container from the second scanning, and comparing the orientation of each of the plurality of packaging elements in the container from the first scanning with the orientation of each of the plurality of packaging elements in the container from the second scanning.

According to an exemplary embodiment of the present invention, a system for detecting package tampering, comprises a first memory and at least one first processor coupled to the first memory, wherein the at least one first processor is configured to scan at a first site a container comprising a packaged item and a plurality of packaging elements surrounding the packaged item, wherein each of the plurality of packaging elements comprises an identification component, and, in performing the scanning at the first site, the at least one first processor is further configured to use the identification component of each of the plurality of packaging elements to detect each of the plurality of packaging elements. The at least one first processor is further configured to determine an orientation of each of the plurality of packaging elements in the container from the scanning at the first site. The system further comprises a second memory and at least one second processor coupled to the second memory, wherein the at least one second processor is configured to scan at a second site the container comprising the packaged item and the plurality of packaging elements surrounding the packaged item, determine an orientation of each of the plurality of packaging elements in the container from the scanning at the second site, and compare the orientation of each of the plurality of packaging elements in the container from the scanning at the first site with the orientation of each of the plurality of packaging elements in the container from the scanning at the second site.

According to an exemplary embodiment of the present invention, a computer program product for detecting package tampering comprises a computer readable storage medium having program instructions embodied therewith, the program instructions executable by one or more processors to cause the one or more processors to perform a method comprising performing first scanning of a container comprising a packaged item and a plurality of packaging elements surrounding the packaged item, wherein each of the plurality of packaging elements comprises an identification component, and the first scanning comprises using the identification component of each of the plurality of packaging elements to detect each of the plurality of packaging elements, determining an orientation of each of the plurality of packaging elements in the container from the first scanning, performing second scanning of the container comprising the packaged item and the plurality of packaging elements surrounding the packaged item, determining an orientation of each of the plurality of packaging elements in the container from the second scanning, and comparing the orientation of each of the plurality of packaging elements in the container from the first scanning with the orientation of each of the plurality of packaging elements in the container from the second scanning.

According to an exemplary embodiment of the present invention, a method for detecting package tampering comprises performing scanning of a container comprising a packaged item and a plurality of packaging elements surrounding the packaged item, wherein each of the plurality of packaging elements comprises an identification component, and the scanning comprises using the identification component of each of the plurality of packaging elements to detect each of the plurality of packaging elements. The method further comprises determining an orientation of each of the plurality of packaging elements in the container from the scanning, and generating an output indicating orientations of the plurality of packaging elements in the container.

According to an exemplary embodiment of the present invention, a method for detecting package tampering comprises performing scanning of a container comprising a packaged item and a plurality of packaging elements surrounding the packaged item, wherein each of the plurality of packaging elements comprises an identification component emitting a signal, determining an orientation of each of the plurality of packaging elements in the container from the scanning, and generating an output indicating orientations of the plurality of packaging elements in the container.

These and other exemplary embodiments of the invention will be described or become apparent from the following detailed description of exemplary embodiments, which is to be read in connection with the accompanying drawings.

BRIEF DESCRIPTION OF THE DRAWINGS

Exemplary embodiments of the present invention will be described below in more detail, with reference to the accompanying drawings, of which.

DETAILED DESCRIPTION

Exemplary embodiments of the invention will now be discussed in further detail with regard to detecting package tampering and, in particular, to using smart packaging elements, such as, for example, packing peanuts or other padded packaging and cushioning material, to generate a unique digital fingerprint corresponding to the package. According to an embodiment, the smart packaging elements each include an identification component integrated with or attached to the smart packaging element. The identification component can include, but is not necessarily limited to, a sensor, a radio frequency identification (RFID) device, such as a nano-RFID device or a device using another type of wireless communication protocol. This invention may, however, be embodied in many different forms and should not be construed as limited to the embodiments set forth herein.

Embodiments of the present invention provide non-invasive detection technology, wherein detection devices are located within the inside of a package. The detection technology, in accordance with embodiments of the present invention, advantageously is capable of indicating if a package has been tampered with and additionally prevents delays through a supply chain.

A packaging method, according to an embodiment of the present invention, utilizes a unique digital fingerprint, as well as a non-invasive detection technique, in order to ensure integrity of a packaged item while the item is delivered using one or more intermediaries. Such secure packaging can be useful in order to combat against counterfeit goods (e.g., medicines), and tampering with other items that need to be transported, for example, across borders and through multiple intermediaries. Embodiments of the present invention may play an important role in developing a robust and trustworthy supply chain solution employing block chain technologies.

An embodiment of the invention uses a large number of soft and tightly packed smart packaging elements (e.g., packing peanuts), with each smart packaging element including a built-in identification component, for example, a sensor or nano-RFID device, and/or devices using another type of wireless communication protocol, such as, but not necessarily limited to, ZigBee®, near field communication (NFC), and Bluetooth®. The smart packaging elements are arranged in a shipping container, such as a box, around a packaged item such that individual packaging elements and their neighbors are uniquely identifiable using a scanner in a non-invasive manner. The electronic identification signals of the packaging elements can be detected by a scanner external to the container to determine the orientation of the packaging elements in the container around the packaged item. The orientation can be referred to herein as a "fingerprint" or "neighborhood map," which is used as the unique fingerprint of the packaged item. The orientation comprises the location of the packaging elements within the package, which can be based on, for example, a side, row and/or column within the package where the packaging elements rest in the package, as well as a position of the packaging elements with respect to other, for example adjacent, packaging elements. If the container is opened and the packaged item is repackaged or moved within the container, the location including the association of the packaging elements with respect to each other will be changed to be different from the unique fingerprint of the packaged item, so that tampering with or replacement of the packaged item can be detected. According to an embodiment, due to a relatively large number of small-sized packaging elements, it will be very hard to achieve the same orientation (i.e., fingerprint) of packaging elements in the container around the packaged item as it was before tampering with the package. As a result, package tampering would be easily identifiable.

A system, in accordance with an embodiment of the present invention, comprises smart packaging elements, such as, but not necessarily limited to, smart packing peanuts that are positioned around a packaged item. The packaging elements can have integrated identification components, such as sensors, nano-RFID devices, devices using another type of wireless communication protocol, or built-in patterns, for example, tiny metallic shapes, that are visible via X-ray or other imaging technique through a container without opening the container. The system also comprises a scanning device, which can be, but is not necessarily limited to, a sensor scanner, an RFID reader, another type of reader compatible with a different wireless communication protocol, or an X-ray or other imaging device, which is configured to determine, without opening the container, the orientation of the packaging elements in the container based on detected identification signals and/or read patterns from the smart packaging elements. Additionally, the system comprises a fingerprint generation module to generate a unique fingerprint of the packaged item based on the detected orientation of the packaging elements when the packaged item is enclosed in the container, and a fingerprint comparison module to compare the orientation of the packaging elements at an intermediate or final destination to determine whether the orientation is the same or similar to the unique fingerprint.

Figure 1:
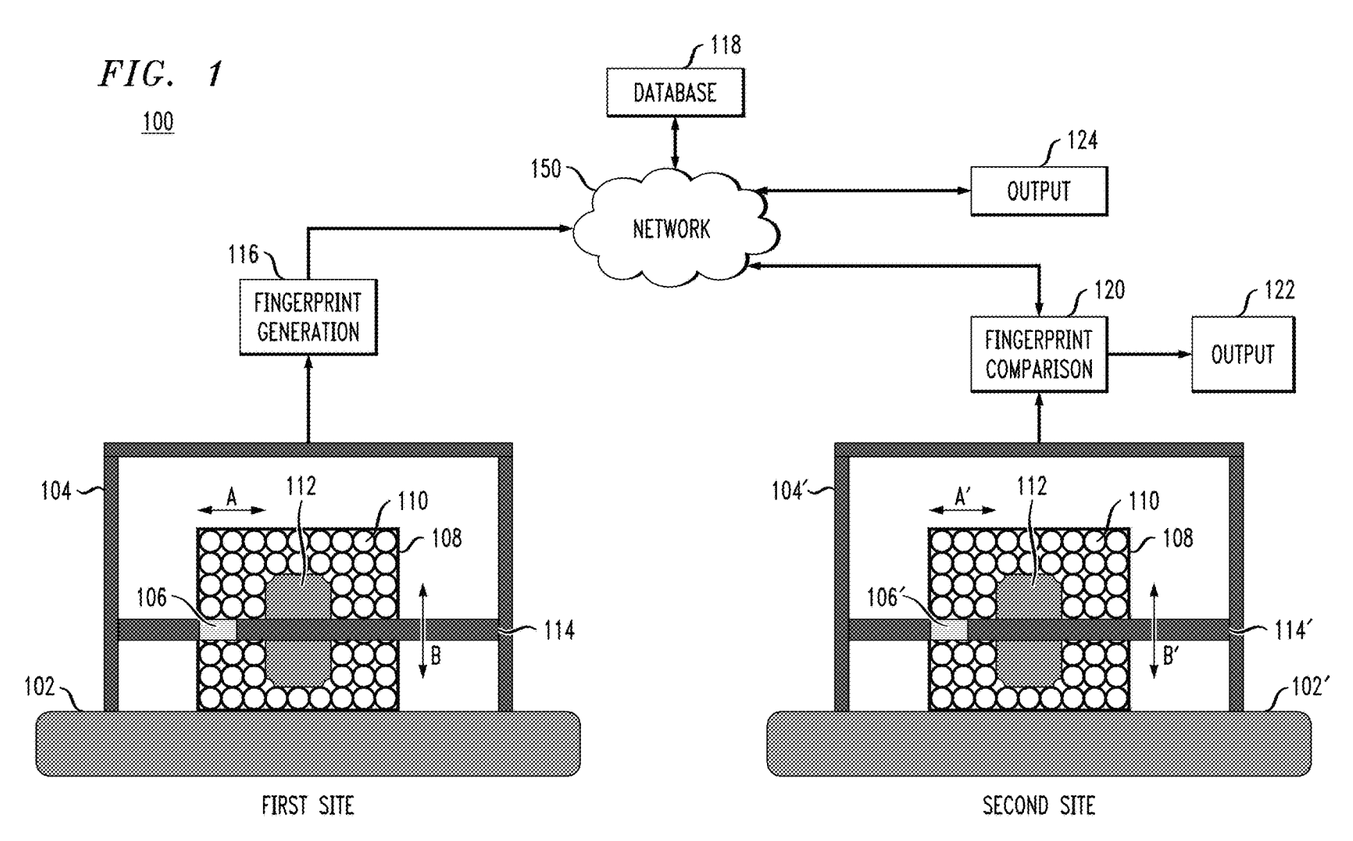
FIG. 1 illustrates a system for detecting package tampering, according to an exemplary embodiment of the present invention.

FIG. 1 illustrates system 100 for detecting package tampering comprising, at a first site, such as, for example, a packaging or origin location, a platform 102 on which scanning device 104 is mounted. Package or container 108 is placed on platform 102 proximate to the scanning device 104. Package 108, for example, a cardboard box or other container, containing a packaged item 112, is tightly packed with smart packaging elements 110 such as, for example, packing peanuts, or other padded packaging and cushioning material, positioned around the packaged item 112. Each smart packaging element 110 includes an identification component, such as, for example, a sensor, nano-RFID device, a device using another type of wireless communication protocol, or a shape or pattern, such as a metallic shape or pattern, which is detectable by an X-ray or other imaging device. In accordance with an embodiment of the present invention, the smart packaging elements 110 are sufficiently small, for example, similar in size to current standard packing peanuts, such that the smart packaging elements 110 are small enough to have a relatively large number of the smart packaging elements 110 in a container, such as a box.

An example architecture of the scanning device 104 is shown in FIG. 1. Such a scanning device 104 includes a probe 106 mounted on a shaft 114, such that the probe 106 and/or shaft 114, controlled by a step-motor, can move horizontally and vertically (see arrows A and B) in small increments in order to scan each side of package 108. The size of the movement increments of the probe 106 and/or shaft 114 can depend on a size of the smart packaging elements 110 and their detection range. For example, depending on the detection range of RFID tags, the increment of movement can be as small as about 1 cm (e.g. for an RFID frequency about 125 KHz or about 13.56 MHz).

According to an embodiment, the scanning device 104 may have multiple probes and shafts like probe 106 and shaft 114 in order to scan multiple sides of a package simultaneously. The area that can be scanned by a probe may not necessarily depend on the size of the probe, since the probe may be detecting electrical identification signals, such as, for example RFID signals, ZigBee®, near field communication (NFC), and Bluetooth® signals. In accordance with an embodiment of the present invention, the scanning device can be a hand held device, such as, but not necessarily limited to, a mobile phone or tablet including an electrical identification signal reader, such as an RFID reader. When using a hand held scanning device, it may be necessary to scan every side of a package to detect electrical identification signals corresponding to smart packaging elements on each side of the package. A fingerprint can include the identifying information of the smart packaging elements in correspondence with the sides of the package on which the smart packaging elements are located and/or the sides of the package from which the electrical identification signals were read.

The scanning device 104 is capable of determining, without opening the package 108, the identity of each of the smart packaging elements 110 and an orientation of the packaging elements 110 in the package 108 based on detected identification signals and/or read patterns of the smart packaging elements 110. The same or similar scanning device 104' is located at a second site, such as for example, a destination or intermediate location. The same or similar components, such as the platform 102', the scanning device 104', the probe 106', the shaft 114' and the arrows A' and B', at the second site are referenced by the same numbers as used at the first site, with the addition of a "prime" (') designation.

The system 100 further comprises a fingerprint generation module 116 operatively connected to the scanning device 104 to generate an output comprising a unique fingerprint of the packaged item based on the determined orientation of the packaging elements 110 when the packaged item 112 is enclosed in the package 108. The unique fingerprint may be stored in a database 118 as corresponding to the packaged item 112, and the database 118 can be operatively connected to the fingerprint generation module 116 via, for example, a direct connection, or via a network 150, for example, the Internet, a local area network, a wide area network and/or a wireless network. The database 118 can store a plurality of unique fingerprints respectively corresponding to a plurality of packaged items that are being shipped.

A fingerprint comparison module 120 at the second site (e.g., an intermediate or destination site) is operatively connected to a scanning device 104' and the database 118 via, for example, network 150. Upon the package 108 arriving at the second site, the scanning device 104', like the scanning device 104, determines, without opening the package 108, the identity of each of the smart packaging elements 110 and an orientation of the packaging elements 110 in the package 108 based on detected identification signals and/or read patterns of the smart packaging elements 110. The fingerprint comparison module 120 generates an output comprising a fingerprint based on the orientation of the packaging elements 110 at an intermediate or final destination, and compares that fingerprint with the unique fingerprint corresponding to the packaged item 112 retrieved from the database 118, and determines whether the fingerprint is the same or similar to the unique fingerprint. The fingerprint comparison module 120 may determine that there was no tampering with, or removal or replacement of the packaged item 112 if the orientation of the packaging elements 110 at the intermediate or final destination is the same or similar enough to the unique fingerprint. Alternatively, the fingerprint comparison module 120 may determine that there was tampering with, or removal or replacement of the packaged item 112 if the orientation of the packaging elements 110 at the intermediate or final destination is different enough from the unique fingerprint. The database 118 can be, for example, from cloud storage.

The system 100, for example, may allow for a minor shifting of one or more packaging elements 110 (e.g., with a predetermined acceptable range of motion, such as, but not necessarily limited to, 0.1 to 0.5 inches, and/or a predetermined acceptable number of packaging elements 110 that move, such as, but not necessarily limited to, 1 to 5 packaging elements) to still allow a determination of no tampering, removal or replacement. However, upon a substantial change in location of one or more packaging elements 110, such as, for example, to a different location beyond the predetermined acceptable range of motion, and/or exceeding the predetermined acceptable number of packaging elements 110 that may move, the system 100 will make a determination of tampering, removal or replacement. Alternatively, the system 100 may interpret any change from the unique fingerprint as tampering, removal or replacement of the packaged item 112. According to an embodiment, in order to reduce the movement of the smart packaging elements in the package, the package can be vacuum sealed.

A determination of tampering, removal or replacement, or of no tampering, removal or replacement of the packaged item 112 can be transmitted from the fingerprint comparison module 120 to output modules 122, 124 via network or non-network connections. The output modules 122, 124 can include, for example, personal computer terminals, and portable devices, such as tablets, mobile phones, laptop computers, which include appropriate interfaces configured to display the determinations. According to an embodiment, the system 100 can include multiple first and second sites depending on the locations from and to which packages may travel during shipping to a location.

According to embodiments of the invention, system 100 is operative to generate fingerprints of the smart packaging elements 110. These fingerprints map the positions of the smart packaging elements 110 within the package 108. According to an embodiment, the fingerprints also include the identity of those smart packaging elements 110, which are neighbors to a packaging element being scanned. In an embodiment of the invention, fingerprints are generated using smart packaging elements with built-in sensors. In this embodiment, the built-in sensors are able to discover other neighbor sensors using sensor network discovery techniques. For example, sensor network discovery techniques can include Internet Protocol version 6 (IPV6) Neighbor Discovery Protocol (NDP) as used for 6LoWPAN (IPV6 over Low power Wireless Personal Area Networks). IPV6 can be defined for low-power and lossy networks (LLNs), such as IEEE 802.15.4.

Figure 2:
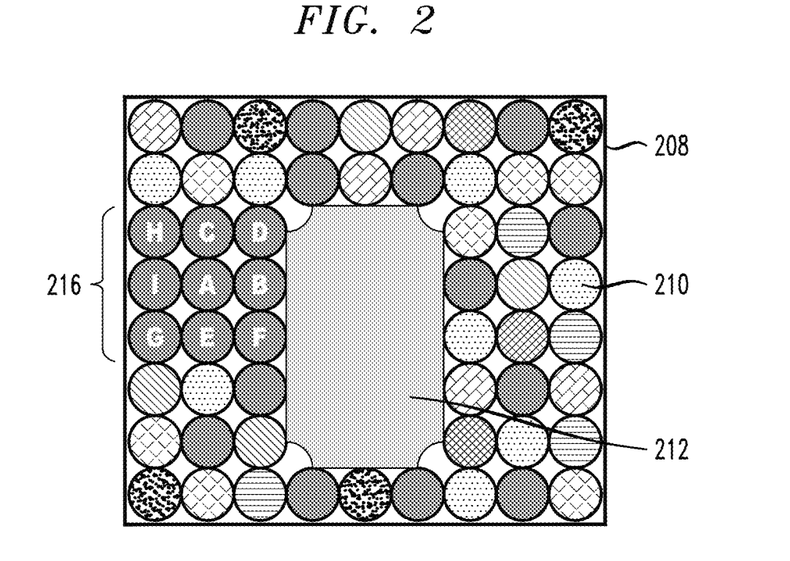
FIG. 2 shows a package including smart packaging elements to illustrate fingerprint generation, according to an exemplary embodiment of the present invention.

In order to generate the fingerprint, in accordance with an embodiment of the present invention, the system could work as follows. Referring, for example, to FIG. 2, a network discovery command is sent to the smart packaging elements 210, each including a sensor, and arranged around packaged item 212. The network discovery command is sent from a scanning device, like scanning device 104, so that the sensors start their network discovery process. Each sensor 210 will have a limited range of visibility such that it can discover only the sensors in close proximity to it, such as, but not necessarily limited to, sensors in adjacent smart packaging elements. After a delay, a query is sent to the sensors to report their neighbors. Thus, the neighbor list of each of the sensors is collected by the scanner. For example, as shown in FIG. 2, sensor A has neighbors C, B, I and E. Sensor B has neighbors A, D and F, and so on. The digital fingerprint of a small set of sensors 216 shown in the example of FIG. 2 has a neighborhood map as follows:

A: C, B, I, E
B: A, D, F
C: H, D, A
D: C, B
E: G, A, F
F: B, E
G: I, E
H: C, I

Such a neighborhood map of the smart packaging elements including, for example, sensors, is generated, for example, as shown above, and used as the fingerprint of the package. The neighborhood map can be more or less comprehensive than what is shown. For example, a neighborhood map can specify every smart packaging element in a package and its neighbors, or a predetermined number of smart packaging elements and their neighbors that is less than all of the smart packaging elements in a package. It may be the case that all packaging elements in a package are smart packaging elements, or that a package include a mixture of smart packaging elements, and conventional packaging elements not including, for example, integrated identification components, such as sensors, nano-RFID devices, devices using another type of wireless communication protocol or built-in patterns.

Figure 3:
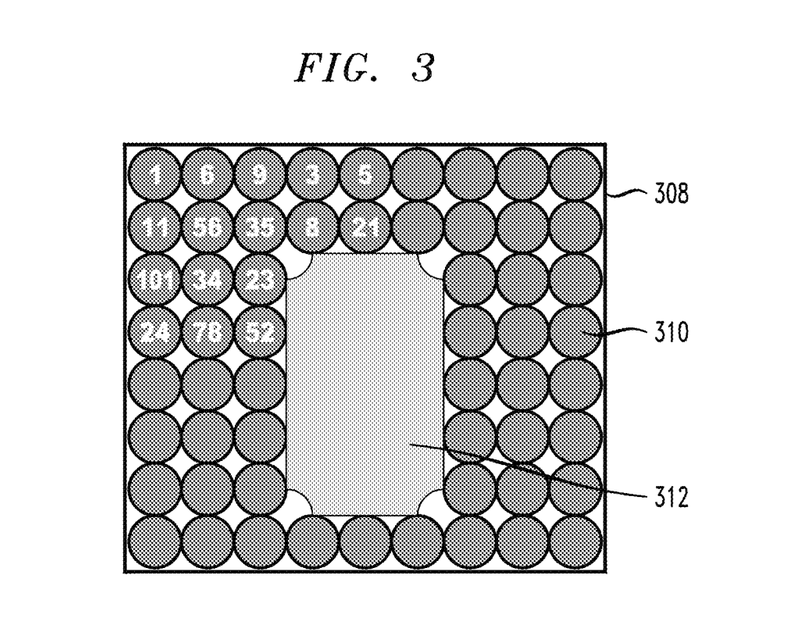
FIG. 3 illustrates fingerprint generation using smart packing elements with built-in RFID tags, according to an exemplary embodiment of the present invention.

According to an embodiment of the present invention, fingerprint generation is achieved using smart packaging elements with built-in RFID devices. Referring to FIG. 3, in this embodiment, the smart packaging elements 310 have built-in RFID tags, and the fingerprint data can be generated as follows. The package 308 is scanned vertically as well as horizontally on one or more sides of the package incrementally with a relatively narrow scanned area such that it does not excite a large number of RFID tags. Depending on the RFID frequency and type, the detection can be done from a distance of about 1 cm to about 6 m. However, with, for example, ZigBee® or Bluetooth® the range can be wider. In addition, there may be other technologies with better resolution.

According to an embodiment, the package 308 is scanned using a scanning device, like scanning device 104, to detect the smart packaging elements, and their orientation around a packaged item 312, including package side, row and column. ID's of the RFID tags are read by the scanning device and associated scanned location (e.g., side, row and column) is stored. Sequences of IDs for rows and columns for each scanned side of the package are then used to generate the fingerprint. Each smart packaging element is scanned by an RFID reader and a map is generated. Referring to FIG. 3, the digital fingerprint of package 308 comprising smart packaging elements 310 including RFID tags around a packaged item 312 may have a fingerprint (neighborhood) map as follows:

Side 1:
Row1: R1, R6, R9, R3, R5 . . .
Row2: R11, R56, R35, R8, R21 . . .
Row3: R101, R34, R23 . . .
Row4: R24, R78, R52 . . .
. . .
Col1: R1, R11, R101, R24 . . .
Col2: R6, R56, R34, R78 . . .
Col3: R9, R35, R23, R52 . . .
. . .

The fingerprint can be more or less comprehensive than what is shown. For example, a fingerprint can specify an orientation of every smart packaging element in a package, or an orientation of a predetermined number of smart packaging elements that is less than all of the smart packaging elements in a package. As noted above, it may be the case that all packaging elements in a package are smart packaging elements, or that a package include a mixture of smart packaging elements, and conventional packaging elements not including, for example, integrated identification components, such as sensors, nano-RFID devices, devices using another type of wireless communication protocol, or built-in patterns.

Figure 4:
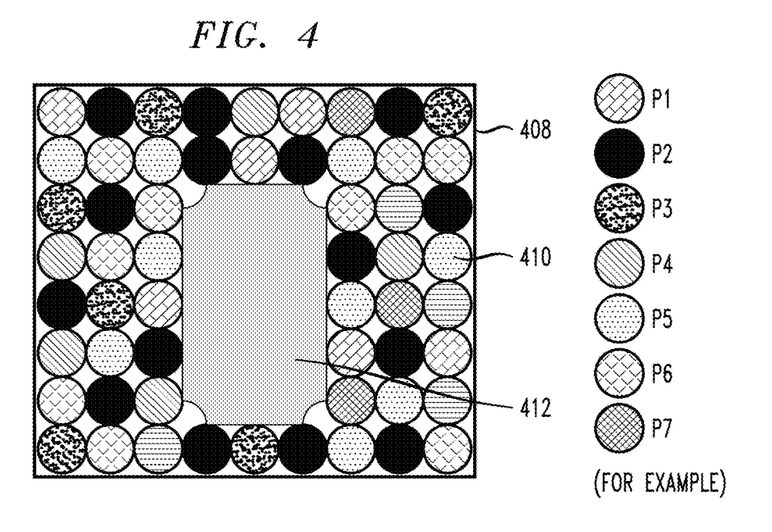
FIG. 4 illustrates fingerprint generation using smart packing elements with built-in patterns, according to an exemplary embodiment of the present invention.

Referring to FIG. 4, according to an embodiment of the present invention, fingerprint generation is achieved using smart packaging elements 410 with built-in patterns visible to an X-ray or other imaging device. In this embodiment, the smart packaging elements 410 may have small metal shapes inside, or a metallic pattern printed on an outside surface of the smart packaging element such that it is visible via an X-ray or other imaging device. The package 408 including the packaged item 412 is scanned vertically as well as horizontally on one or more sides of the package. Metal patterns formed inside or outside of the smart packaging elements 410 are then identified using image processing of an X-ray image or image from another imaging device. Each packaging element 410 is scanned by an X-ray or other imaging medium, and the different patterns are retrieved. Identified patterns and associated scanned locations including the side, row and column are stored. Sequences of patterns for rows and columns for each scanned side of the package 408 are then used to generate the fingerprint. An example of the fingerprint data (neighborhood map) generated is shown below:

Side 1:
Row1: P1, P2, P3, P2, P4 . . .
Row2: P5, P6, P5, P2 . . .
Row3: P3, P2, P6 . . .
Row4: P4, P6, P5 . . .
. . .
Col1: P1, P5, P3, P4 . . .
Col2: P2, P6, P2 . . .
Col3: P3, P5, P6 . . .
. . .

Side 2:
Row1: P2, P36, P10, P31, P4 . . .
Row2: P98, P4, P9, P54 . . .
Row3: P101, P34, P23 . . .
Row4: P21, P78, P56, P90 . . .
Col1: P2, P98, P101, P21 . . .
Col2: P36, P4, P34 . . .
Col3: P10, P9, P23 . . .

Here "P" represents "pattern." FIG. 4 includes example pattern IDs for clarity.

The fingerprint can be more or less comprehensive than what is shown. For example, a fingerprint can specify an orientation of every smart packaging element in a package, or an orientation of a predetermined number of smart packaging elements that is less than all of the smart packaging elements in a package. As noted above, it may be the case that all packaging elements in a package are smart packaging elements, or that a package include a mixture of smart packaging elements, and conventional packaging elements not including, for example, integrated identification components, such as sensors, nano-RFID devices, devices using another type of wireless communication protocol, or built-in patterns. According to an embodiment, a package may also include a mixture of different smart packaging elements using different identification components.

Advantageously, the digital fingerprint generation of a package, in accordance with embodiments of the present invention, can be used in connection with detecting package tampering. According to an embodiment, each entity that handles a package, for example, the sender and intermediate authorized personnel, will receive one or more digital keys in order to be granted access to generate a package fingerprint or perform a fingerprint comparison. Such keys can be, for example, private and public-key pairs for an entity. A sender can generate a package fingerprint and sign-off using the sender's private key in order to ensure that the fingerprint was generated by the sender and not an unauthorized party. Such a fingerprint can be stored in a database, for example, in cloud storage, such as block chain or traditional cloud storage, such that the fingerprint is retrievable later.

According to an embodiment, the fingerprint can be hashed so that the actual fingerprint data, including the orientation of the smart packaging elements, is not decodable. Such an un-decodable format of a fingerprint would ensure that even with very sophisticated instruments, for example robots, the orientation of the smart packaging elements cannot be easily obtained by potential hackers. If the fingerprint is stored in an un-decodable format, compromising the fingerprint would require testing a large number of combinations of the smart packaging elements, which would likely not be cost effective for potential hackers.

As noted above, a system may require an absolute match to a fingerprint to prevent a tampering determination, where not a single smart packaging element can be moved or go undetected because of machine error or due to disturbances during transportation, such as, for example, shaking. Alternatively, as noted above, a system can specify a threshold, for example >95% match of the fingerprint, in order to allow for a certain amount of machine error during the detection of the fingerprint at the receiver side and/or disturbances which may alter the position of the smart packaging elements during transportation. According to an embodiment, depending on whether all sides of a package are scanned, which can vary, especially in the case of a hand-held scanning device, electrical identification signals of smart packaging elements, such as, for example, RFIDs, may only be detected on select sides of a package. In this case, a relatively lower threshold for a fingerprint match, for example, >60% match, may suffice to conclude that no tampering occurred. Such functionality may be useful if, for example, a user decides to scan less than a total package on receipt, so that a match with an original fingerprint based on a full scan at shipping, may be relatively lower.

According to an embodiment, a receiver scans a package and gathers the package fingerprint data in the same way as the sender. The receiver can extract the sender's fingerprint using the sender's public-key. The sender's fingerprint is then compared with the detected fingerprint at the receiver side. The comparison can be performed using different techniques depending on how the sender's fingerprint was sent. For example, according to an embodiment, if the fingerprint is hashed, devices on the receiver end will then need to also hash the detected fingerprint in order to compare it to the sender's fingerprint. An entity may also choose not to hash, but rather store the fingerprint in a decodable format. As discussed above, in the case of an exact match, it is assumed that the scanning of the package can be done without moving the smart packaging elements, and that none of the smart packaging elements moved during transport.

Alternatively, if a matching threshold has been provided, the receiver would check whether there is a match of the compared package fingerprints that is above the given threshold. For example, given a threshold of 95%, there must be a minimum of a 95% match of the package fingerprints at the sender and receiver sides.

According to an embodiment, if a package is opened and repackaged by authorized personnel, for example a customs agent at an intermediate point, the package fingerprint will be re-generated for the repackaged item and signed-off by the authorized personnel's private key. To detect tampering, the receiver will then compare the fingerprint at the receiver site with this new fingerprint corresponding to the repackaged item rather than the original fingerprint signed-off by the sender. Thus, throughout a supply chain, a receiver can compare the detected fingerprint at the receiver site with the most recent fingerprint generated by the sender or intermediate authorized personnel before confirming safe delivery. If any actionable discrepancy in the fingerprint is detected, a notification (e.g., tampering notification) is automatically generated, and necessary actions are taken, such as applying penalties and/or notifying the sender and/or receiver.

As noted above, a mix of traditional packaging elements and the smart packaging elements of the embodiments may be used. Use of a mixture of traditional packaging elements and the smart packaging elements may reduce cost and potentially achieve similar results to prevent tampering as described above. In other embodiments, smart packaging elements can be colored and the box/container can be transparent such that the colored packaging elements are visible from the outside and a pattern of the packaging elements is detectable. Additionally, packaging elements comprising sensors may comprise various types of sensors including, but not necessarily limited to, temperature sensors, humidity sensors and pressure sensors.

Figure 5:
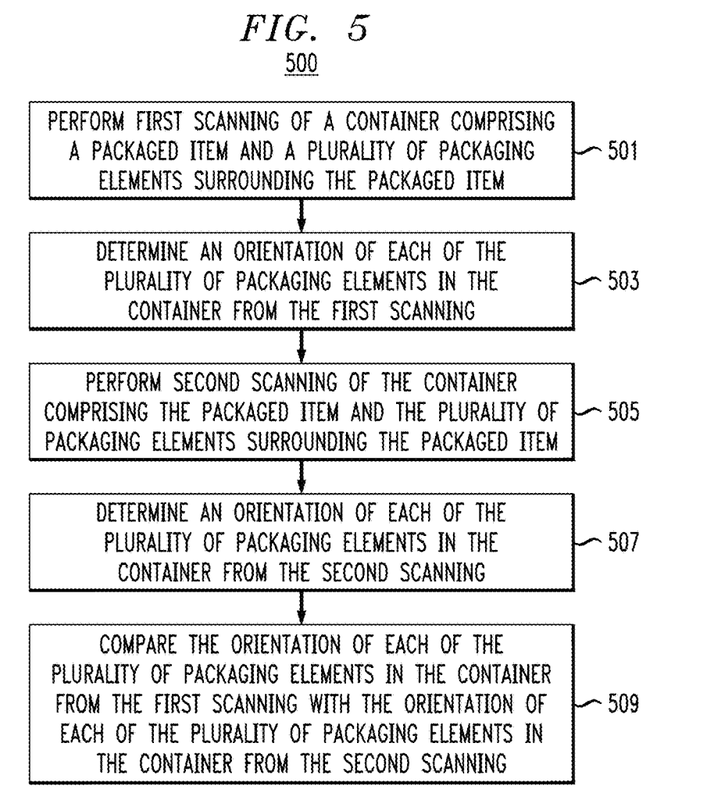
FIG. 5 is a flow diagram of a process for detecting package tampering, according to an exemplary embodiment of the invention.

FIG. 5 is a flow diagram of a process for detecting package tampering, according to an exemplary embodiment of the invention. Referring to FIG. 5, the process 500 includes, at block 501, performing first scanning of a container comprising a packaged item and a plurality of packaging elements surrounding the packaged item. Each of the plurality of packaging elements are smart packaging elements comprising an identification component, such as, for example, a sensor, an RFID tag, a device using another type of wireless communication protocol, or a pattern detectable by an imaging device, such as a metallic pattern detectable by an X-ray device. A sensor identification component of a first packaging element is configured to discover a sensor identification component of a second packaging element using network discovery techniques as explained herein.

The first scanning comprises using the identification component of each of the plurality of packaging elements to detect each of the plurality of packaging elements. According to an embodiments, identification components can generate various forms of a unique identifiers that are unique, for example, globally or per a manufacturer. Such an identifier can be generated using, for example, a standardized scheme, for example Electronic Product Code (EPC), as done with RFID tags.

The process 500 further includes, at block 503, determining an orientation of each of the plurality of packaging elements in the container from the first scanning. Referring to blocks 505 and 507, a second scanning of the container comprising the packaged item and the plurality of packaging elements is performed, and an orientation of each of the plurality of packaging elements in the container from the second scanning is determined. The process 500 further includes, at block 509, comparing the orientation of each of the plurality of packaging elements in the container from the first scanning with the orientation of each of the plurality of packaging elements in the container from the second scanning.

The first scanning and the second scanning are non-invasive, being performed when the container is closed and/or sealed, and can be performed at respective first and second sites, such as, for example, a packaging or sending site, and an intermediate or receiver site.

The process may further include generating first and second outputs indicating orientations of the plurality of packaging elements in the container from the first and second scanning, respectively. The first output can be compared with the second output, and a conclusion can be formed whether package tampering occurred based on a result of the comparing. For example, it may be determined that there is a difference between the orientation of each of the plurality of packaging elements in the container from the first scanning and the orientation of each of the plurality of packaging elements in the container from the second scanning. According to an embodiment, the determined difference is compared to a threshold value to determine whether package tampering occurred. Alternatively, any detected difference may lead to a conclusion of package tampering.

Embodiments of the present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 6:
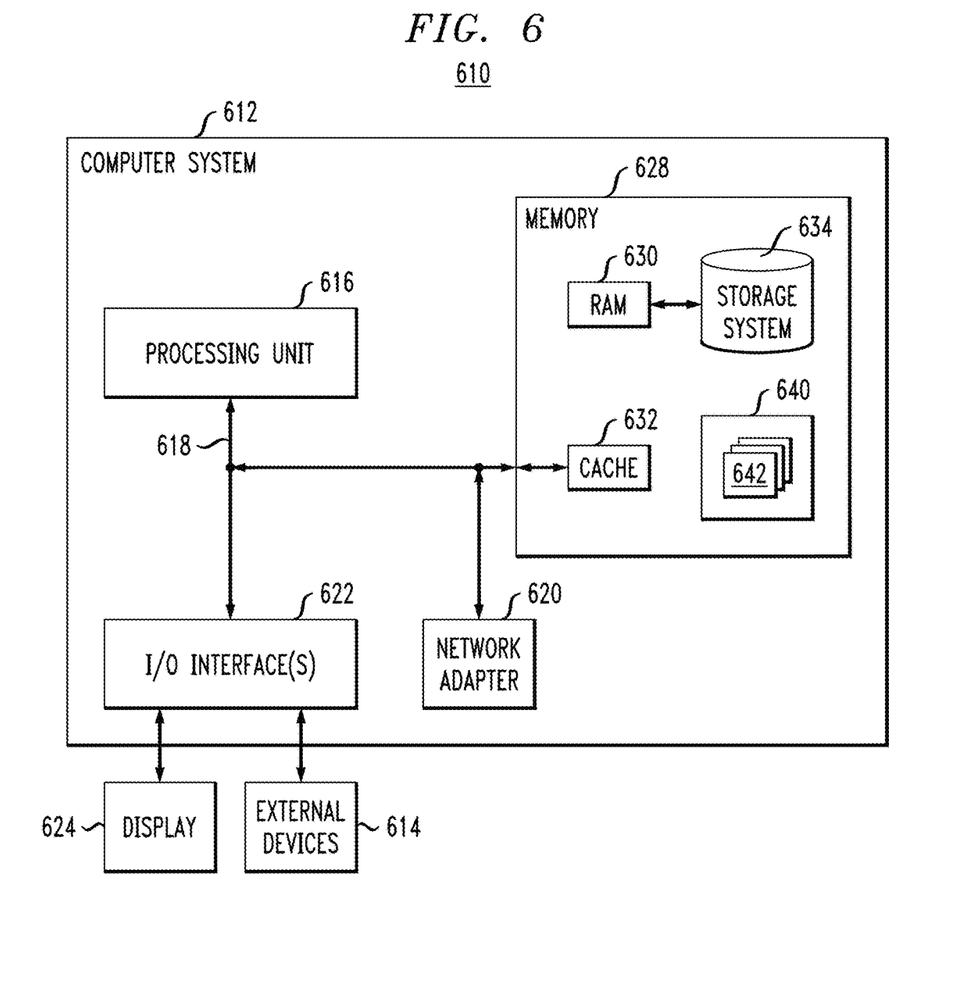
FIG. 6 illustrates a computer system in accordance with which one or more components/steps of the techniques of the invention may be implemented, according to an exemplary embodiment of the invention.

One or more embodiments can make use of software running on a general-purpose computer or workstation. With reference to FIG. 6, in a computing node 610 there is a computer system/server 612, which is operational with numerous other general purpose or special purpose computing system environments or configurations. Examples of well-known computing systems, environments, and/or configurations that may be suitable for use with computer system/server 612 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 612 may be described in the general context of computer system executable instructions, such as program modules, being executed by a computer system. Generally, program modules may include routines, programs, objects, components, logic, data structures, and so on that perform particular tasks or implement particular abstract data types. Computer system/server 612 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 6, computer system/server 612 in computing node 610 is shown in the form of a general-purpose computing device. The components of computer system/server 612 may include, but are not limited to, one or more processors or processing units 616, a system memory 628, and a bus 618 that couples various system components including system memory 628 to processor 616.

The bus 618 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system/server 612 typically includes a variety of computer system readable media. Such media may be any available media that is accessible by computer system/server 612, and it includes both volatile and non-volatile media, removable and non-removable media.

The system memory 628 can include computer system readable media in the form of volatile memory, such as random access memory (RAM) 630 and/or cache memory 632. The computer system/server 612 may further include other removable/non-removable, volatile/nonvolatile computer system storage media. By way of example only, storage system 634 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 618 by one or more data media interfaces. As depicted and described herein, the memory 628 may include at least one program product having a set (e.g., at least one) of program modules that are configured to carry out the functions of embodiments of the invention. A program/utility 640, having a set (at least one) of program modules 642, may be stored in memory 628 by way of example, and not limitation, as well as an operating system, one or more application programs, other program modules, and program data. Each of the operating system, one or more application programs, other program modules, and program data or some combination thereof, may include an implementation of a networking environment. Program modules 642 generally carry out the functions and/or methodologies of embodiments of the invention as described herein.

Computer system/server 612 may also communicate with one or more external devices 614 such as a keyboard, a pointing device, a display 624, etc., one or more devices that enable a user to interact with computer system/server 612, and/or any devices (e.g., network card, modem, etc.) that enable computer system/server 612 to communicate with one or more other computing devices. Such communication can occur via Input/Output (I/O) interfaces 622. Still yet, computer system/server 612 can communicate with one or more networks such as a local area network (LAN), a general wide area network (WAN), and/or a public network (e.g., the Internet) via network adapter 620. As depicted, network adapter 620 communicates with the other components of computer system/server 612 via bus 618. It should be understood that although not shown, other hardware and/or software components could be used in conjunction with computer system/server 612. Examples, include, but are not limited to: microcode, device drivers, redundant processing units, external disk drive arrays, RAID systems, tape drives, and data archival storage systems, etc.

It is understood in advance that although this disclosure includes a detailed description on cloud computing below, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Computing node 610 in FIG. 6 can be an example of a cloud computing node. Computing node 610 is only one example of a suitable cloud computing node and is not intended to suggest any limitation as to the scope of use or functionality of embodiments of the invention described herein. Regardless, computing node 610 is capable of being implemented and/or performing any of the functionality set forth hereinabove. It is also to be understood that computing node 610 is not necessarily a cloud computing node.

Figure 7:
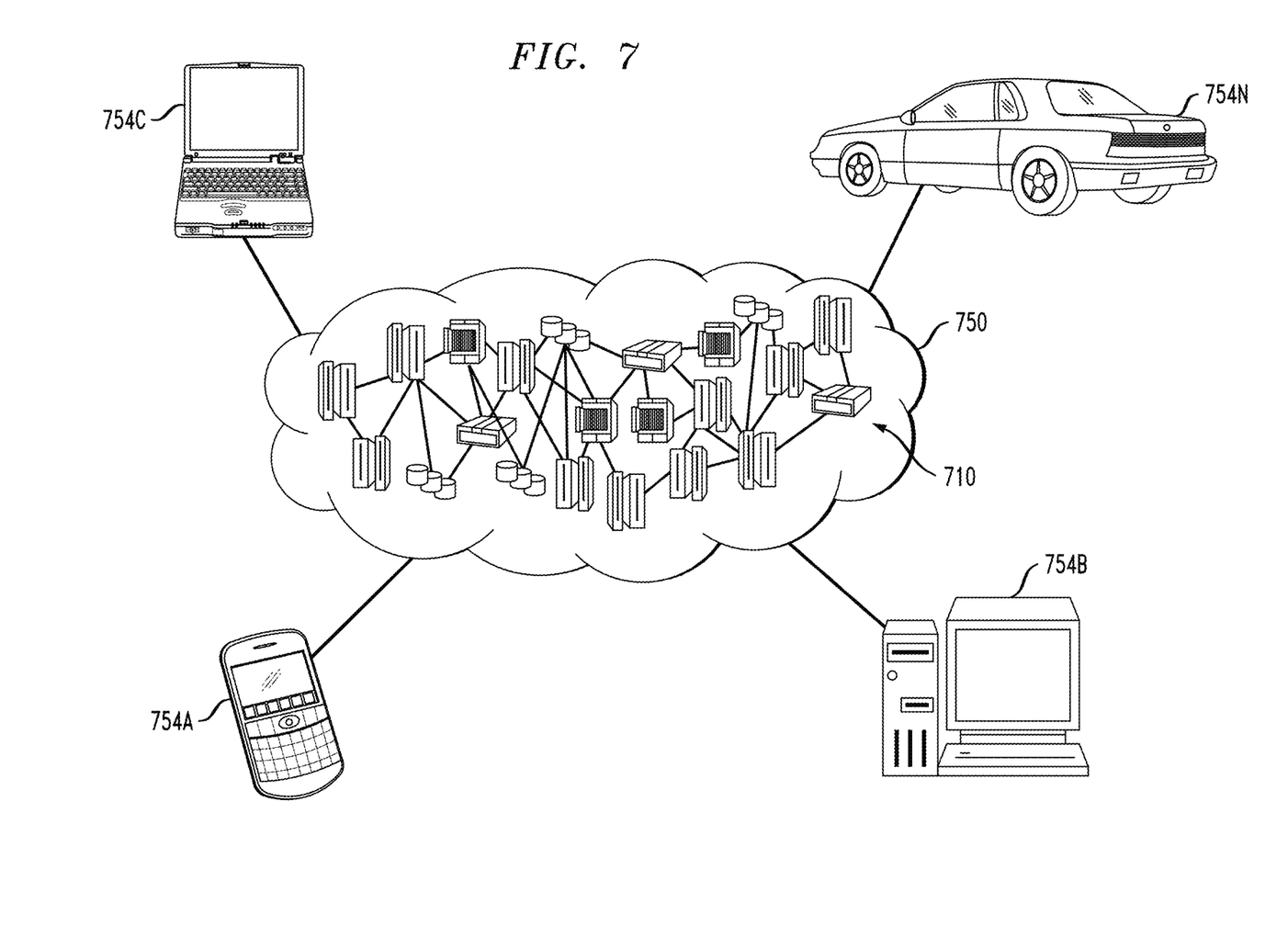
FIG. 7 depicts a cloud computing environment, according to an exemplary embodiment of the present invention.

Referring now to FIG. 7, illustrative cloud computing environment 750 is depicted. As shown, cloud computing environment 750 comprises one or more cloud computing nodes 710 with which local computing devices used by cloud consumers, such as, for example, a wearable device (not explicitly shown), a personal digital assistant (PDA) or cellular telephone 754A, desktop computer 754B, laptop computer 754C, and/or automobile computer system 754N may communicate. Nodes 710 may communicate with one another. They may be grouped (not shown) physically or virtually, in one or more networks, such as Private, Community, Public, or Hybrid clouds as described hereinabove, or a combination thereof. This allows cloud computing environment 750 to offer infrastructure, platforms and/or software as services for which a cloud consumer does not need to maintain resources on a local computing device. It is understood that the types of computing devices 754A-N shown in FIG. 7 are intended to be illustrative only and that computing nodes 710 and cloud computing environment 750 can communicate with any type of computerized device over any type of network and/or network addressable connection (e.g., using a web browser).

Figure 8:
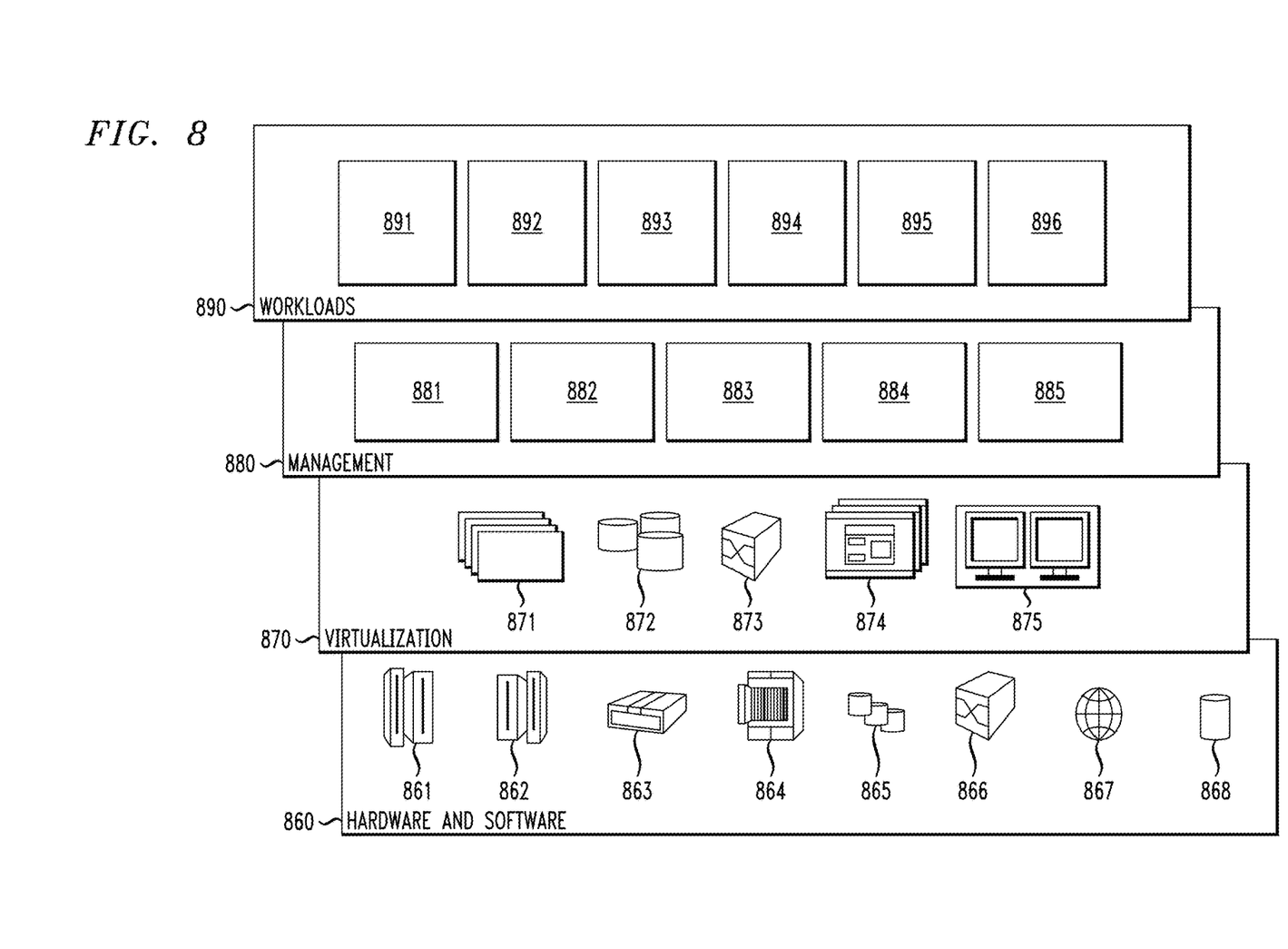
FIG. 8 depicts abstraction model layers, according to an exemplary embodiment of the invention.

Referring now to FIG. 8, a set of functional abstraction layers provided by cloud computing environment 750 (FIG. 7) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 860 includes hardware and software components. Examples of hardware components include: mainframes 861; RISC (Reduced Instruction Set Computer) architecture based servers 862; servers 863; blade servers 864; storage devices 865; and networks and networking components 866. In some embodiments, software components include network application server software 867 and database software 868.

Virtualization layer 870 provides an abstraction layer from which the following examples of virtual entities may be provided: virtual servers 871; virtual storage 872; virtual networks 873, including virtual private networks; virtual applications and operating systems 874; and virtual clients 875.

In one example, management layer 880 may provide the functions described below. Resource provisioning 881 provides dynamic procurement of computing resources and other resources that are utilized to perform tasks within the cloud computing environment. Metering and Pricing 882 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 883 provides access to the cloud computing environment for consumers and system administrators. Service level management 884 provides cloud computing resource allocation and management such that required service levels are met. Service Level Agreement (SLA) planning and fulfillment 885 provide pre-arrangement for, and procurement of, cloud computing resources for which a future requirement is anticipated in accordance with an SLA.

Workloads layer 890 provides examples of functionality for which the cloud computing environment may be utilized. Examples of workloads and functions which may be provided from this layer include: mapping and navigation 891; software development and lifecycle management 892; virtual classroom education delivery 893; data analytics processing 894; transaction processing 895; and fingerprint generation and comparison, and package tampering determination 896, which may implement the functionality described above with respect to FIGS. 1-7.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A method for detecting package tampering, comprising:
    performing first scanning of a container comprising a packaged item and a plurality of packaging elements surrounding the packaged item, wherein:
        each packaging element of the plurality of packaging elements is a container filling element comprising an identification device integrated therewith and transmitting an identification signal;
    determining a first orientation of the plurality of packaging elements in the container from the first scanning;
    performing second scanning of the container comprising the packaged item and the plurality of packaging elements surrounding the packaged item;
    determining a second orientation of the plurality of packaging elements in the container from the second scanning; and
    comparing the first orientation with the second orientation;
    wherein the first scanning and the second scanning are respectively performed when the container is closed with a first scanning device external to the container and a second scanning device external to the container;
    wherein the first scanning and the second scanning comprise using a plurality of the identification signals transmitted from the integrated identification devices of the plurality of packaging elements to detect the plurality of packaging elements;
    wherein determining the first and second orientations comprises mapping locations of the plurality of packaging elements within the container based on the plurality of the identification signals; and
    wherein the method is performed by at least one computer system comprising at least one memory and at least one processor coupled to the memory.

2. The method according to claim 1, wherein the identification device of the plurality of packaging elements is selected from the group consisting of a sensor and a radio frequency identification (RFID) tag.

3. The method according to claim 2, wherein a sensor identification device of a first packaging element is configured to discover a sensor identification device of a second packaging element.

4. The method according to claim 1, further comprising generating a first output indicating the first orientation of the plurality of packaging elements in the container.

5. The method according to claim 4, further comprising generating a second output indicating the second orientation of the plurality of packaging elements in the container.

6. The method according to claim 5, wherein the comparing comprises comparing the first output with the second output.

7. The method according to claim 1, further comprising concluding whether the package tampering occurred based on a result of the comparing.

8. The method according to claim 1, further comprising determining a difference between the first orientation and the second orientation.

9. The method according to claim 8, further comprising comparing the difference to a threshold value to determine whether the package tampering occurred.

10. The method according to claim 1, wherein the first scanning is performed at a first site and the second scanning is performed at a second site.

11. A system for detecting package tampering, comprising:
    a first memory and at least one first processor coupled to the first memory, wherein the at least one first processor is configured to:

scan at a first site a container comprising a packaged item and a plurality of packaging elements surrounding the packaged item, wherein:
  each packaging element of the plurality of packaging elements is a container element comprising an identification device integrated therewith and transmitting an identification signal; and
  determine a first orientation of the plurality of packaging elements in the container from the scanning at the first site; and
a second memory and at least one second processor coupled to the second memory, wherein the at least one second processor is configured to:
  scan at a second site the container comprising the packaged item and the plurality of packaging elements surrounding the packaged item;
  determine a second orientation of the plurality of packaging elements in the container from the scanning at the second site; and
  compare the first orientation with the second orientation;
wherein the scanning at the first and second sites are respectively performed when the container is closed with a first scanning device external to the container and a second scanning device external to the container;
wherein, in performing the scanning at the first and second sites, the at least one first processor and the at least one second processor are further configured to use a plurality of the identification signals transmitted from the integrated identification devices of the plurality of packaging elements to detect the plurality of packaging elements; and
wherein, in determining the first and second orientations, the at least one first processor and the at least one second processor are further configured to map locations of the plurality of packaging elements within the container based on the plurality of the identification signals.

12. The system according to claim 11, wherein the identification device of the plurality of packaging elements is selected from the group consisting of a sensor and a radio frequency identification (RFID) tag.

13. The system according to claim 11, wherein the at least one first processor is further configured to generate a first output indicating the first orientation of the plurality of packaging elements in the container.

14. The system according to claim 13, wherein the at least one second processor is further configured to generate a second output indicating the second orientation of the plurality of packaging elements in the container.

15. The system according to claim 14, wherein in comparing the at least one second processor is further configured to compare the first output with the second output.

16. The system according to claim 11, wherein the at least one second processor is further configured to conclude whether the package tampering occurred based on a result of the comparing.

17. A computer program product for detecting package tampering, the computer program product comprising a computer readable storage medium having program instructions embodied therewith, the program instructions executable by one or more processors to cause the one or more processors to perform a method comprising:
  performing first scanning of a container comprising a packaged item and a plurality of packaging elements surrounding the packaged item, wherein:
    each packaging element of the plurality of packaging elements is a container filling element comprising an identification device integrated therewith and transmitting an identification signal;
  determining a first orientation of the plurality of packaging elements in the container from the first scanning;
  performing second scanning of the container comprising the packaged item and the plurality of packaging elements surrounding the packaged item;
  determining a second orientation of the plurality of packaging elements in the container from the second scanning; and
  comparing the first orientation with the second orientation;
  wherein the first scanning and the second scanning are respectively performed when the container is closed with a first scanning device external to the container and a second scanning device external to the container;
  wherein the first scanning and the second scanning comprise using a plurality of the identification signals transmitted from the integrated identification devices of the plurality of packaging elements to detect the plurality of packaging elements; and
  wherein determining the first and second orientations comprises mapping locations of the plurality of packaging elements within the container based on the plurality of the identification signals.

18. A method for detecting package tampering, comprising:
  performing scanning of a container comprising a packaged item and a plurality of packaging elements surrounding the packaged item, wherein:
    each packaging element of the plurality of packaging elements is a container filling element comprising an identification device integrated therewith and transmitting an identification signal; and
    the scanning comprises using a plurality of the identification signals transmitted from the integrated identification devices of the plurality of packaging elements to detect the plurality of packaging elements;
  determining an orientation of the plurality of packaging elements in the container from the scanning; and
  generating an output indicating the orientation of the plurality of packaging elements in the container;
  wherein the scanning is performed when the container is closed with a scanning device external to the container;
  wherein determining the orientation comprises mapping locations of the plurality of packaging elements within the container based on the plurality of the identification signals; and
  wherein the method is performed by at least one computer system comprising at least one memory and at least one processor coupled to the memory.

19. The method according to claim 18, further comprising storing the output indicating the orientation of the plurality of packaging elements in a database.

20. The method according to claim 19, further comprising:
  performing an additional scanning of the container comprising the packaged item and the plurality of packaging elements surrounding the packaged item;
  determining an orientation of the plurality of packaging elements in the container from the additional scanning;
  generating an additional output indicating the orientation of the plurality of packaging elements in the container from the additional scanning;

retrieving the stored output from the database; and
comparing the stored output with the additional output to determine whether there are any differences between the stored output and additional output.

21. The method according to claim 20, further comprising concluding whether the package tampering occurred based on a result of the comparing.

22. A method for detecting package tampering, comprising:
performing scanning of a container comprising a packaged item and a plurality of packaging elements surrounding the packaged item, wherein each packaging element of the plurality of packaging elements is a container filling element comprising an identification device integrated therewith and emitting an identification signal;
determining an orientation of the plurality of packaging elements in the container from the scanning; and
generating an output indicating the orientation of the plurality of packaging elements in the container;
wherein the scanning is performed when the container is closed with a scanning device external to the container;
wherein determining the orientation comprises mapping locations of the plurality of packaging elements within the container based on a plurality of the identification signals transmitted from the integrated identification devices of the plurality of packaging elements; and
wherein the method is performed by at least one computer system comprising at least one memory and at least one processor coupled to the memory.

* * * * *